US00PP31292P3

(12) United States Plant Patent
Aguas-Alvarado

(10) Patent No.: US PP31,292 P3
(45) Date of Patent: Dec. 31, 2019

(54) BLACKBERRY PLANT NAMED 'MM01'

(50) Latin Name: ***Rubus* L. subgenus *Rubus* Watson.**
Varietal Denomination: MM01

(71) Applicant: Mario Aguas-Alvarado, Freedom, CA (US)

(72) Inventor: Mario Aguas-Alvarado, Freedom, CA (US)

( * ) Notice: Subject to any disclaimer, the term of this patent is extended or adjusted under 35 U.S.C. 154(b) by 0 days.

(21) Appl. No.: 15/932,950

(22) Filed: May 26, 2018

(65) Prior Publication Data

US 2018/0352694 P1 Dec. 6, 2018

Related U.S. Application Data

(60) Provisional application No. 62/606,426, filed on Sep. 21, 2017, provisional application No. 62/603,489, filed on Jun. 1, 2017.

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP17,162 | P3 | 10/2006 | Clark |
| PP22,449 | P3 | 1/2012 | Clark |
| PP23,497 | P3 | 3/2013 | Clark |
| PP27,401 | P3 | 11/2016 | Clark |

*Primary Examiner* — Anne Marie Grunberg
(74) *Attorney, Agent, or Firm* — Phase M Legal

(57) ABSTRACT

The invention relates to a new and distinct cultivar of lightly thorned blackberry plant named 'MM01' having a strong plant vigor and moderate post-harvest reddening. The new variety 'MM01' produces a heavy primocane fruit crop and an economically viable floricane fruit crop.

6 Drawing Sheets

Latin name of the genus and species:

Botanical classification: *Rubus* L. subgenus *Rubus* Watson.

VARIETY DENOMINATION

The new blackberry variety denomination is 'MM01'.

BACKGROUND OF THE INVENTION

Blackberries (*Rubus* subgenus *Rubus* Watson) are a well-known, aggregate fruit generally popular throughout the world. Traditional blackberry plants produce small dark black clusters of fruit once per season on second-year cane growth known as floricanes. The plants are often thorn bearing varieties with various spines along the canes which hinder fruit harvest and plant maintenance. More recent breeding efforts have led to the development of primocane-fruiting blackberries which produce fruit on first year canes (i.e. primocanes) as well as second-year floricanes. Such primocane-fruiting blackberries generally produce fruit in late summer to autumn, whereas floricane-fruiting types commonly bear fruit in early to mid-summer. The additional extended harvest season for primocanes offers fresh market growers a significant economic advantage over more typical floricane-fruiting cultivars.

One example of an existing primocane-fruiting blackberry variety is 'APF-122', U.S. Plant Pat. No. 27,401, which has a very firm round small fruit size (5.8 g on average) and a significantly early fruiting season (average ripe fruit date for primocanes on 'APF-122' is 5-6 months after planting). 'Reuben', U.S. Plant Pat. No. 23,497, is another example of a primocane blackberry, although not generally grown in California. 'Reuben' has much larger fruits than 'APF-122', averaging 14.5 g versus 5.8 g, respectively. The fruits of 'Reuben' are oblong and blocky, while fruits of 'APF-122' are round. Also, 'Reuben' is a late-fruiting primocane variety, compared to the early fruiting season of 'APF-122'.

The present invention comprises a new and distinct lightly thorned cultivar of primocane blackberry referred to by the cultivar name 'MM01'. The new variety, only lightly thorned, was originally identified as selection no. MA10-05, and originated from a cross made by Mario Aguas-Alvarado in a controlled breeding program in Freedom, Calif. USA. 'MM01' was initially believed to be fully thorn-less but successive generations have shown a few thorns at the base, less thorns on the midpoint and no thorns at the terminal point of the canes. The male parent of the new variety is variety known as 'Navaho', U.S. Plant Pat. No. 6,679 and the female parent is the variety known as 'APF45', U.S. Plant Pat. No. 22,449. The new variety 'MM01' has been asexually reproduced by vegetative side shoot in Freedom, Calif., and the distinguishing characteristics are retained through successive generations of asexual reproduction.

BRIEF SUMMARY OF THE INVENTION

'MM01' is a distinctive primocane blackberry variety with a moderately to heavy fruit size and a relatively early primocane fruiting season. Other distinctive characteristics of 'MM01' include very little thorns and a strong plant vigor with good adaptability to multiple microclimates.

COMPARISON WITH PARENT VARIETIES

Plants of the new blackberry variety 'MM01' are similar to the male parent 'Navaho' in plant vigor, heavy fruit crop, higher soluble solids, and adaptability to microclimates. Under commercial practice with similar growing conditions in Freedom, Calif., plants of the new blackberry variety 'MM01' compared to plants of the male parent 'Navaho' in the following characteristics:

1. The new variety 'MM01' produces fruit as primocane and floricane whereas the male parent 'Navaho' produces fruit as floricane only.
2. The new variety 'MM01' has very few thorns for primocanes and floricanes whereas 'Navaho' has no thorns.

Plants of the new blackberry variety 'MM01' are similar to the female parent 'APF-45' in plant vigor and adaptability to microclimates. With similar growing conditions in Salinas, Calif., under commercial practice, plants of the new blackberry variety 'MM01' compared to plants of the female parent 'APF-45' in the following characteristics:

1. The new variety 'MM01' produces heavier primocane fruit than the female variety 'APF-45' (8.2 g vs. 4.3-5.2 g on average, respectively).
2. The new variety 'MM01' is only lightly thorned while 'APF-45' has thorns.

COMPARISON WITH OTHER KNOWN VARIETIES

Compared to 'APF-122', the present cultivar, 'MM01', differs with a larger primocane fruit size (8.2 g vs. 5.5 g, on average) and significantly later fruiting season (average ripe fruit date for primocanes on 'APF-122' is 5-6 months after planting vs. 7-8 months after planting on 'MM01'). In addition, 'MM01' has the significant advantage of having very few thorns while 'APF-122' has spines on floricanes and primocanes.

Compared to 'Reuben', a variety not generally available in California, the primocane fruits of 'Reuben' are much larger than 'MM01', averaging 14.5 g versus 8.2 g, respectively. Also, 'Reuben' is a late-fruiting variety, while 'MM01' is considered early for a primocane-fruiting type. The fruits of 'Reuben' are oblong and blocky, while fruits of 'MM01' are generally round. 'Reuben' is also a thorny variety while 'MM01' is only lightly thorned.

BRIEF DESCRIPTION OF ILLUSTRATIONS

Typical specimens of the plant, flowers, and fruit of the new blackberry variety 'MM01' are shown in the accompanying photographs. The colors shown are as true as possible within the usual limits of this kind of illustration.

DETAILED DESCRIPTION OF THE NEW CULTIVAR

Figure 1:
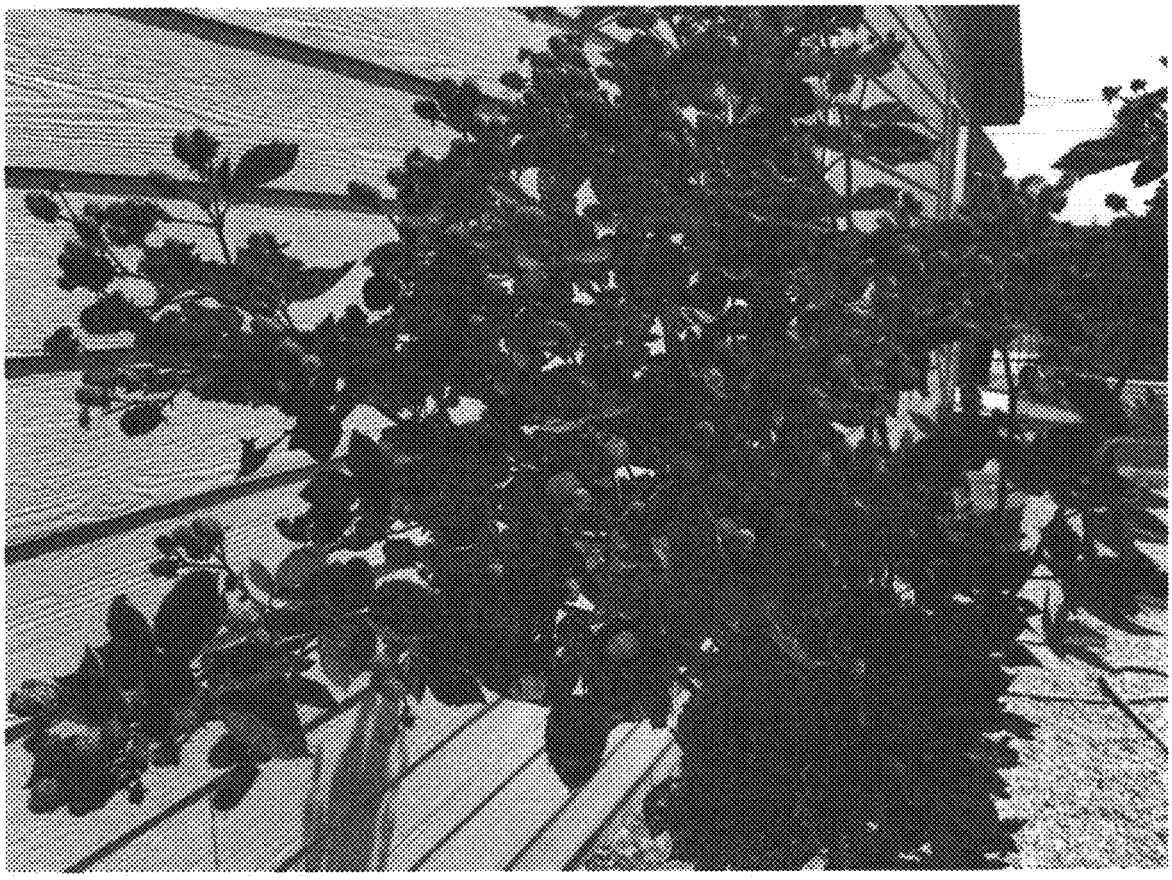
FIG. 1 is a photograph showing fruit of the new blackberry cultivar 'MM01' at the ripening stage, along with crop load on one-year old canes. The photo was taken of plants having a crown aged of 6 years and cane age of 7 months.
Figure 2:
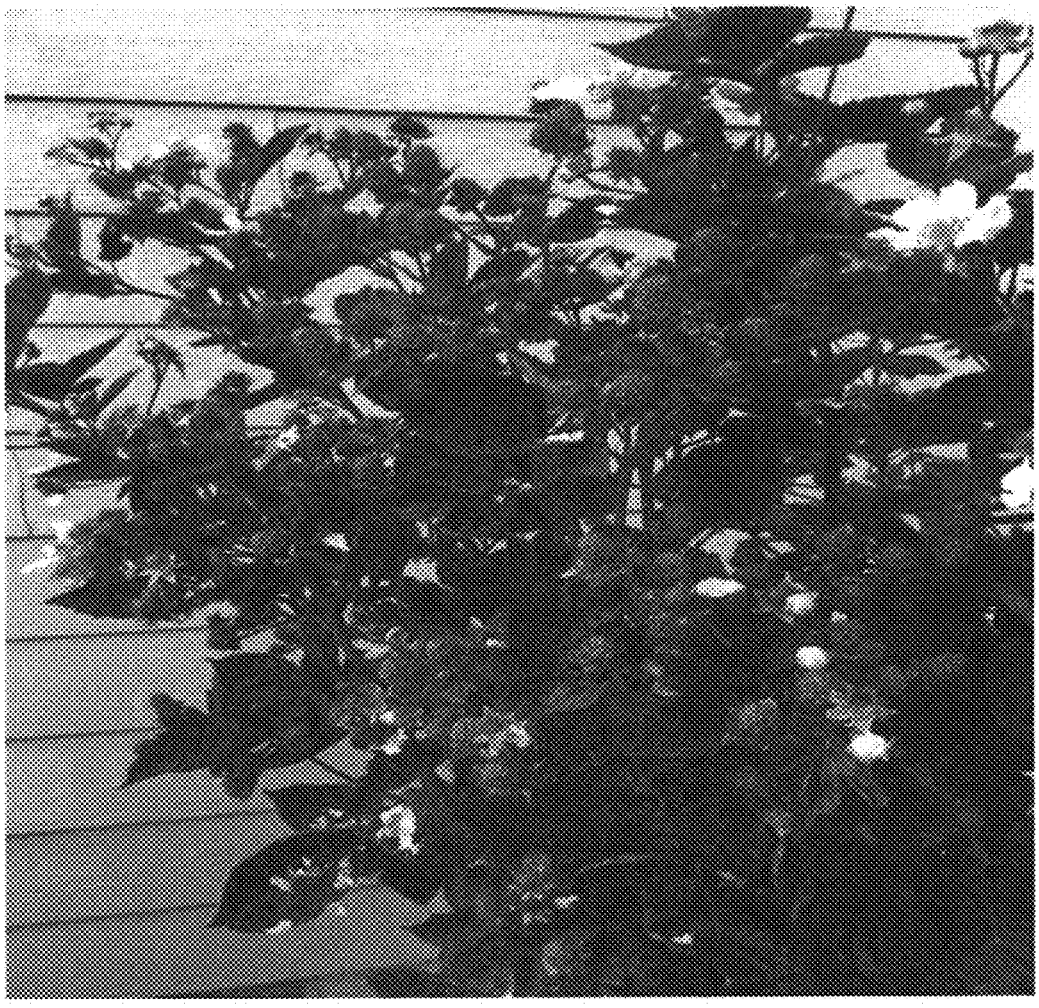
FIG. 2 is a photograph showing the full plant of the new blackberry cultivar 'MM01' at the green fruit stage. The photo was taken of plants having a crown aged of 6 years and cane age of 8 months.
Figure 3:
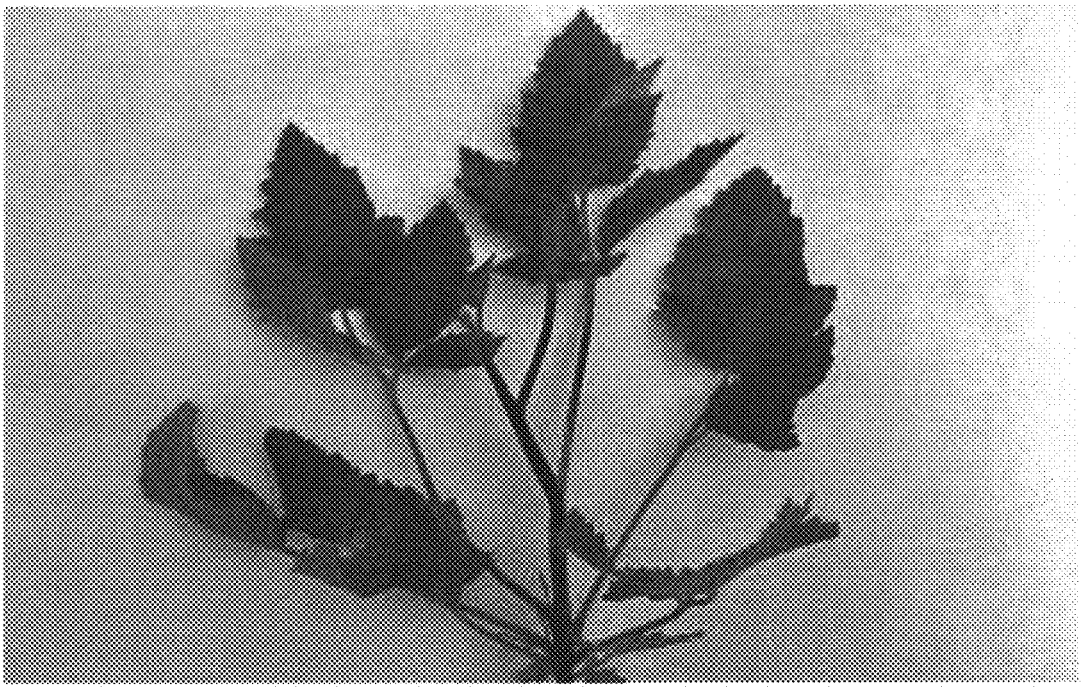
FIG. 3 is a photograph showing an exemplary branch of the new blackberry cultivar 'MM01'.
Figure 4:
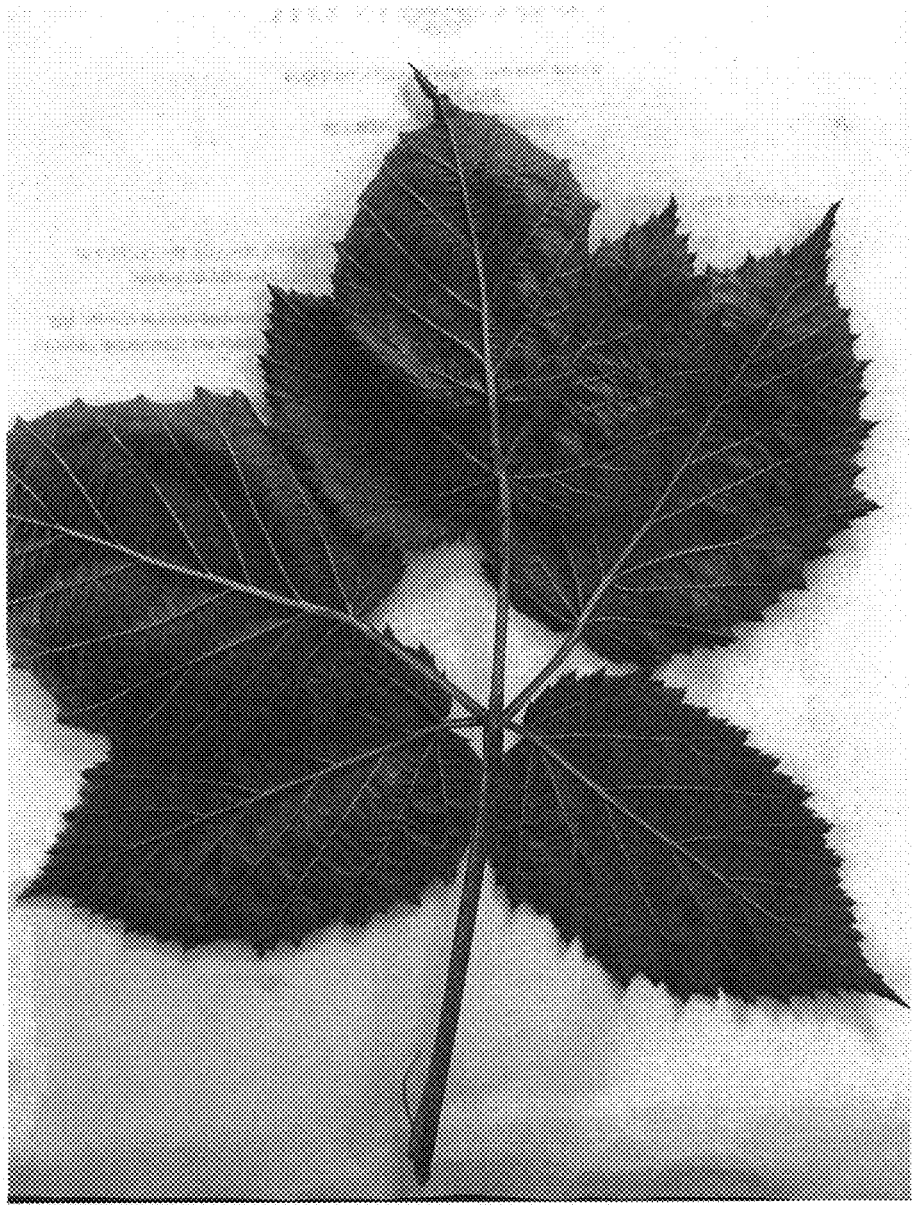
FIG. 4 is a photograph showing exemplary primocane leaves of the new blackberry cultivar 'MM01'.
Figure 5:
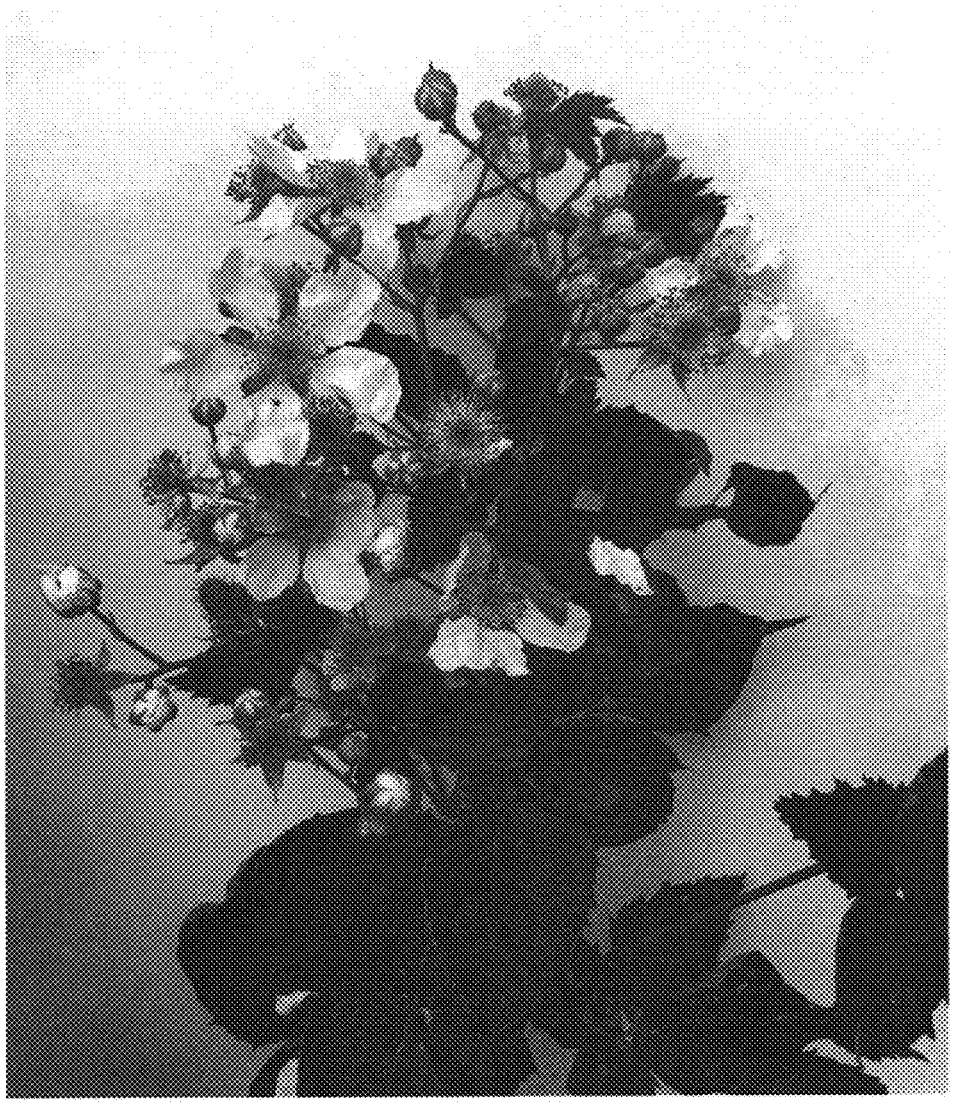
FIG. 5 is a photograph showing an exemplary flower cluster of the new blackberry cultivar 'MM01'.
Figure 6:
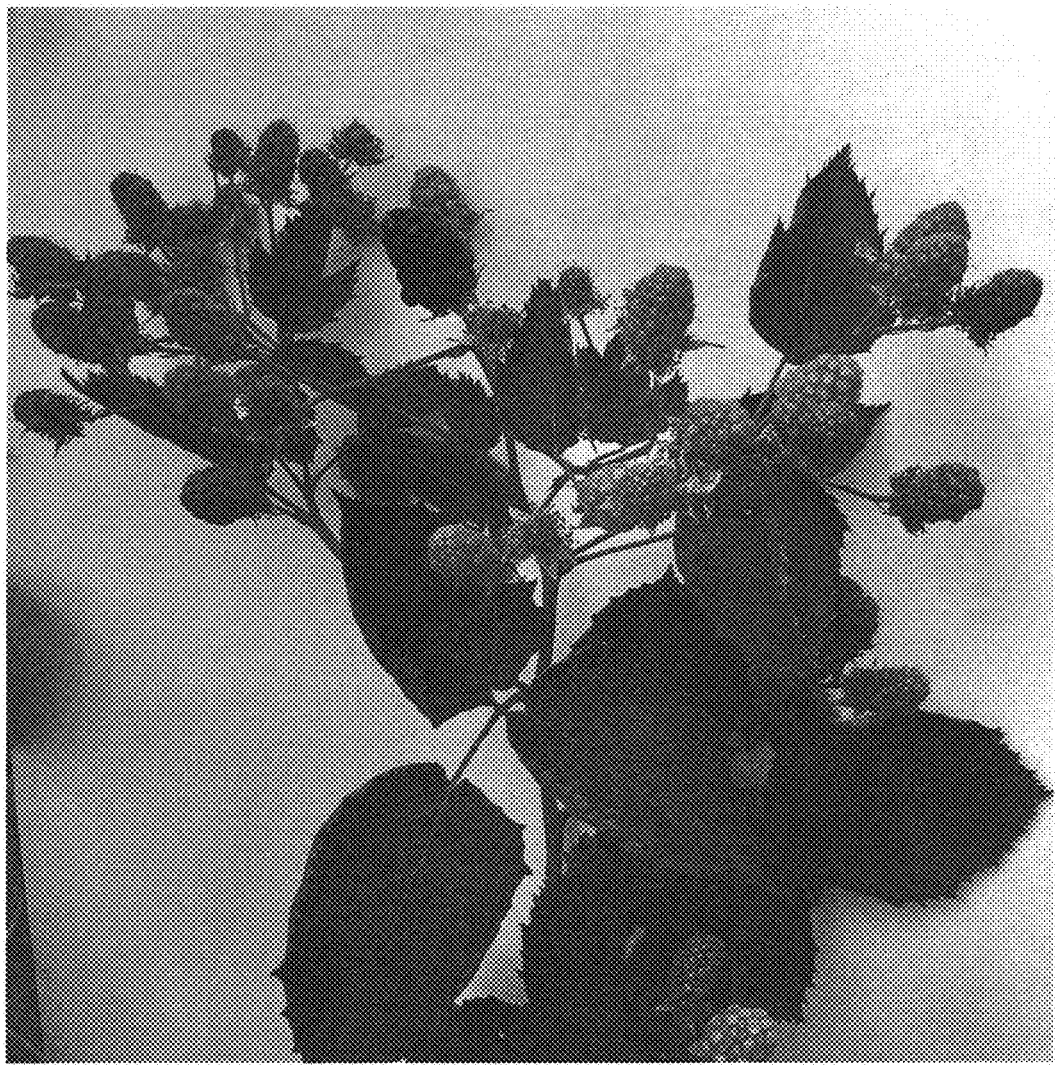
FIG. 6 is a photograph of an exemplary branch with green fruit showing the productivity of the new blackberry cultivar 'MM01'.

The following detailed description sets forth the distinctive characteristics of 'MM01'. The data which define these characteristics were collected from asexual reproductions carried out in Freedom, Calif. Plants used for botanical data were six-year-old plants in June 2017 grown in sandy loam soil with trickle irrigation. The plants were fertilized near bud break with complete or nitrogen fertilizer, and had an additional nitrogen fertilizer application. Weeds were controlled with pre- and post-emergence herbicides supplemented with mechanical weed control activities. A single application of liquid lime sulfur was applied to the plants at bud break, but no other fungicides were used.

Color designations, color descriptions, and other phenotypical descriptions may deviate from the stated values and descriptions depending upon variation in environmental, seasonal, climatic and cultural conditions. 'MM01' has not been observed under all possible environmental conditions. Color references are to The Royal Horticultural Society Colour Chart, London (R.H.S.) (2007 edition). The sizes, dimensions, colors, and other characteristics are approximations and averages.

Plant:

General description: Plants of the new cultivar 'MM01' are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are lightly thorned in primocanes and floricanes. When propagated from roots, the new shoots are thornier than the basal shoots.

Actively growing canes tend to shift from vegetative to reproductive state at approximately 1 m in height and require pinching. Canes have an erect growth habit, even in Year 1, and are of medium to large stature. The height averages 1.5 m as measured from cane base to cane apex. Root growth in spring and summer is fibrous and spreading to the width of the aerial canopy, generally with a 75:25 ratio of brown lignified coarse roots and off-white fine (feeder) roots, respectively.

Primocane berries of 'MM01' are medium-large and round in shape, but sometimes develop a slightly elongated shape. Primocane fruit is generally bright glossy black in color, and very attractive. Primocane fruit averaged 8.2 g/berry. The fresh fruit rates very good in flavor, sweet and mildly acidic, with a distinct blackberry aroma.

Primocane fruit and flowers are borne on the cane terminus or on lateral branches if primocanes are tipped, and fruiting continues down the primocane during the season. The number of nodes down the cane that develop flowers is largely dependent on the length and conditions of the late summer to fall growing period. The fruit is good for fresh market use with keeping quality and shipping quality that appear excellent.

Floricane fruit is similar in shape and color to the primocane crop and is sufficiently heavy to be an economically viable floricane crop.

'MM01' plants have strong vegetative vigor and an erect growth habit. Primocanes emerge both from the crown of the plant as well as from the roots (as suckers). Productivity is high. 'MM01' is considered economically viable under commercial production systems in California. Natural branching occurs but is variable. Canes are lightly thorny and erect.

Cold hardiness: Unknown.

Plant:

*Size*.—Plants are grown in hedgerows and primocanes are tipped at 45 to 55 inches approx. Plant range size from 1.20 to 2.5 meters high and 40 to 60 cm wide.

*Growth habitat*.—Canes erect; moderated vigor; suckers from crown and roots.

*Growth rate*.—Primocanes reach tipping in early April depending on pruning date.

*Productivity*.—Floricane. 1.5 to 2.5 kg per plant, which is higher than known varieties 'APF45' and 'APF122'. Primocane. 3 to 4 kg per plant, which is higher than known variety 'APF122' and similar to known variety 'APF45'.

*Canes*.—Lightly Thorny, Erect. Floricane. Cane diameter: base 2.10 cm; mid-point 1.20 cm; terminal 0.95 cm. Internode length: base 6.5 cm; midpoint 5.2 cm; terminal; 3.74. Floricane color: base: Yellow Green Group (148A); midpoint: Yellow Green Group (148B); terminus: Yellow Green Group (148B). Canes are rounded to angular in cross-section with branches distributed only on upper third. Thorn density (per 30 cm): base 4; midpoint 2; terminus 1 and in most occasions terminus is completely thorn-less. Cane thorn length: 3.5 mm; non-curved. Primocanes (current season cane). Cane diameter: base 1.75 cm; midpoint 1.4 cm; terminal 0.91 cm. Internode length: base 13.0 cm; midpoint 8.2 cm; terminal 2.5 cm. Primocane color: base: Green Group (147A); midpoint Green Group (147B); terminus Green Group (148A). Three new canes in most plants but up to five in some occasions. Primocanes have an angular cross-section with branches from the bottom and up to mid-section in most cases if left un-tipped. If tipped, canes branch immediately from upper third of plant. Thorn density (per 30 cm): base 4; midpoint 2; terminus 1 and in most occasions terminus is completely thorn-less. Thorn length: 3.5 mm; non-curved. Young shoots show a medium number of hairs.

Foliage:

*Primocane*.—Leaves — Large mature compound leaf Width 24.15 cm; Length 17.50 cm. Leaflet — Width: 15.55 cm; Length: 16.25 cm; shape ovate, acuminate apex and rounded base; margin serrated; margin: 0.40 cm and 0.30 cm wide; pubescence very light on both abaxial and adaxial surfaces; number of leaflets per compound leaf 5 and occasionally up to 7. Terminal leaflet is v-shaped in cross-section with a medium degree of blistering between the veins. Color — Base axial: Yellow Green Group (139A); abaxial Green Group (138A) Petioles — Length: 90 cm; color: Yellow Green Group (139C); Texture smooth. Petiolules — Length 50 cm; color: Yellow Green Group (139C); texture smooth. Stipules — Length 1.14 cm; Width 0.15 cm; Texture smooth.

*Floricane*.—Leaves — Medium mature compound leaf Width 14.5; Length: 17.0 cm. Leaflet — Width: 6.40 cm; Length: 8.90 cm; shape ovate with acuminate apex and rounded base; margin serrated; serrated teeth length: 0.30 cm; width at base: 0.40 cm; pubescence on both axial and abaxial; number of leaflet per compound leaf is 3 and in some occasions up to 5. Terminal leaflet is v-shaped in cross-section with a medium degree of blistering between veins. Color — Base abaxial: Yellow Green Group (139A); midpoint abaxial: Yellow Green Group (139B); adaxial: Green Group (138A). Petioles — Length: 3.70 cm; color: Yellow Green Group (139C); texture smooth. Petiolules — Length: 0.50 cm; color: Yellow Green Group (139C); texture smooth. Stipules — Length: 0.70 cm; Width: 0.15 cm; texture smooth.

Flowers:

*Floricane*.—Date of bloom — 10% bloom April 25; 50% bloom May 5; last bloom June 5. Petal color — White Group (NN155). Reproductive Organs — Stamens — erect, numerous. Pistils — numerous. Pollen — normal and abundant. Flower diameter — 3.65 cm. Petal Size — Length: 1.97 cm; Width: 1.30 cm. Average flowers per cluster — 9.5. Average petals per flower — 5 to 6. Number of sepals per flower — 5 to 6. Peduncle color — Yellow Green Group (144A). Cyme Type — elongate simple. Cyme Length — average: 105 cm and up to 130 cm.

*Primocanes*.—First bloom — May 15 and depending on planting or pruning date. Petal color — White Group (NN155). Reproductive organs — Stamens; numerous. Pistils; numerous. Pollen: abundant and fertile during normal conditions. Flower diameter — 3.70 cm. Petal Size — Length: 2.10 cm; Width: 1.4 cm. Average flowers per cluster — 19 under tunnel culture. Average petals per flower — 5. Number of sepals per flower — 5 to 6. Peduncle Length — 2.7 cm. Peduncle color — Yellow Green Group (144B). Cyme Type — Simple elongated. Cyme Length — 120 cm and up to 160 cm.

Fruit:

*Floricane*.—Maturity — First: June 6 under normal conditions; fruiting period up to 60 days. Size — Medium-large, average: 7 to 8 g. Diameter of primary fruit — Equator: 2.43 cm; base pole: 1.90 cm; terminal pole: 1.68 cm. Diameter of secondary fruit — Equator: 1.99 cm; base pole: 1.13 cm. Shape — Elongated to blocky. Color — Black Group (203B) Drupelet size — 0.46 cm; number per fruit 75-85. Solubles solids — 9.9%. Fruit uses — Fresh market.

*Primocane*.—Maturity — July 30 on mature plants. Size — Large; above 8 g in Freedom, Calif. Diameter of primary fruit — Equator: 2.15 cm; base pole: 2.20 cm; terminal pole 1.71 cm. Diameter of secondary fruit — Equator: 1.95 cm; base pole: 1.93 cm; terminal pole: 1.63 cm. Length — Primary fruit: 2.85 cm. Shape — Elongated to blocky. Color — Black Group (203B). Drupelet Size — 0.6 cm; number of drupelets per fruit 95-105. Soluble Solids — 10%. Fruit Use — Fresh Market.

What is claimed is:

1. A new and distinct variety of blackberry plant, substantially as described and illustrated herein.

* * * * *